United States Patent [19]

Hammond et al.

[11] 4,430,433

[45] Feb. 7, 1984

[54] PRODUCTION OF ARYL ACYLAMIDASES

[75] Inventors: Peter M. Hammond, Melton Mowbray; Christopher P. Price, Stapleford; Michael D. Scawen, Salisbury, all of England

[73] Assignee: Public Health Laboratory Service Board, London, England

[21] Appl. No.: 326,275

[22] Filed: Dec. 1, 1981

[30] Foreign Application Priority Data

Dec. 2, 1980 [GB] United Kingdom ............... 8038633

[51] Int. Cl.³ .................. C12N 9/80; C12N 1/20; C12R 1/39; C12R 1/40
[52] U.S. Cl. .................. 435/228; 435/253; 435/815; 435/876; 435/877
[58] Field of Search ................... 435/228, 253

[56] References Cited

PUBLICATIONS

Engelhardt et al., Applied Microbiology, vol. 26, No. 5, pp. 709–718 (1973).
Hsiung et al., Biochemical and Biophysical Research Communications, vol. 66, No. 4, pp. 1225–1230 (1975).

*Primary Examiner*—Lionel M. Shapiro

[57] ABSTRACT

A process for the production of an aryl acylamidase enzyme involves culturing bacteria of one of the strains *Pseudomonas fluorescens* ATCC 39005 (or suitable mutants or variants thereof) or *Pseudomonas putida* ATCC 39004 (or suitable mutants or variants thereof) in a culture medium in which the bacterial strains produce aryl acylamidase and collecting the enzyme containing material, generally the cell material. Preferably the resulting cells are then disrupted, especially by enzymatic treatment, and the aryl acylamidase is separated from the other unwanted substances, generally the other cell constituents.

Preferably the culture medium contains N-acylaniline, especially N-acetyl aniline. The N-acylaniline may form part of a complex or defined salts medium.

26 Claims, No Drawings

PRODUCTION OF ARYL ACYLAMIDASES

The present invention relates to the production of aryl acylamidase enzymes and to microorganisms capable of producing said enzymes.

The aryl acylamidase enzymes referred to herein are defined by the International Union of Biochemistry (Enzyme Nomenclature 1978, Academic Press, New York, 1979) as those enzymes which catalyse the hydrolysis of anilides to anilines plus fatty acid anions. These enzymes are given the number EC 3.5.1.13 by the IUB.

The enzymic deacylation of anilides (N-acylanilines) has been known for many years to occur in mammalian tissues. Early studies reported the hydrolysis of acetanilide and phenacetin by extracts of liver and kidney taken from rabbit and the rapid deacylation of acetylsulphanilamides by chick kidney homogenates.

Similar enzymic reactions have been shown to take place in plant tissues. For example an aryl acylamidase was isolated from rice plants whilst propanil, 3,4-dichloropropionanilide, was hydrolysed by the extracts of dandelion roots.

Micro-organisms have been less widely investigated as a source of such enzymes. The majority of studies on microbial amidases have been concerned with aliphatic substrates, in particular formamide (Hynes and Pateman, *J. Gen. Microbiol.*, (1970), 63, 317), acetamide (Jakoby and Fredericks, *J. Biol. Chem.*, (1964), 234, 1978) and propionamide (Kelly and Clarke, *J. Gen. Microbiol.*, (1962), 27, 305). The latter amidase, from *Pseudomonas aeruginosa,* hydrolyses a range of short chain aliphatic amides. Further study of this microorganism, however, showed that mutant variants of the strain produce an amidase which allows the bacterium to utilise an N-acylaniline substrate (Brown and Clarke, *J. Gen. Microbiol.,* (1972), 70, 287).

The occurrence of microbial acylamidases specific for an aromatic substrate have been investigated to a lesser extent. The majority of such reports have arisen as a result of the study of herbicide transformations. Such aryl acylamidases have been demonstrated in *Pseudomonas striata* grown on isopropyl N-(3-chlorophenyl) carbamate (Kearney, *J. Agric. Food Chem.,* (1965), 13, 561), Penicillium grown on Karsil, N-(3,4-dichlorophenyl)-2-methylpentanamide (Sharabi and Bordeleau, *App. Microbiol.*, (1969), 18, 369), *Bacillus sphaericus* grown on Linuron, 3-(3,4-dichlorophenyl-1-methoxy-1-methylurea (Engelhardt et al., *App. Microbiol.,* (1973), 26, 709), and *Chaetomium globosum* grown on Alachlor, 2-chloro-N-(2,6-diethylphenyl)-N-methoxymethyl acetamide (Tiedje et al., *J. Agric. Food Chem.,* (1975), 23, 77).

The growth of microorganisms on N-acylaniline substrates has also been reported. For example, a strain of *Pseudomonas acidovorans,* isolated from soil, was shown to grow on phenacetin (N-acetyl-4-ethoxyaniline) and acetanilide (Alt et al., *J. Gen. Microbiol.,* (1975) 87 260). Similarly a culture of *Pseudomonas striata* grew on acetanilide (Hsiung et al., *Biochem, Biophys. Res. Commun.,* (1975), 66, 1225). In these cases the culture was shown to produce an aryl acylamidase.

The present invention provides a novel method for producing aryl acylamidase enzymes which not only employs novel aryl acylamidase producing microorganisms but also, for the first time, yields aryl acylamidases of high activity, in high yield and in large quantity.

According to the present invention there is provided a process for producing an aryl acylamidase enzyme which comprises culturing bacteria of one of the strains *Pseudomonas fluorescens* NCIB 11615 deposited at the National Collection of Industrial Bacteria (NCIB), Aberdeen, Scotland on Oct. 8, 1980 (equivalent to *Pseudomonas fluorescens* ATCC 39005 deposited at the American Type Culture Collection (ATCC), Maryland, U.S.A. on Nov. 19, 1981) or aryl acylamidase producing mutants or variants thereof, or *Pseudomonas putida* NCIB 11616 deposited at NCIB, Aberdeen, Scotland, on Oct. 8, 1980 (equivalent to *Pseudomonas putida* ATCC 39004 deposited at ATCC, Maryland, U.S.A. on Nov. 19, 1981) or aryl acylamidase producing mutants or variants thereof, in a culture medium in which said bacterial strains are capable of producing aryl acylamidase and collecting the aryl acylamidase enzyme containing material. The enzyme containing material may be the cell material, the cell supernatant or both. When the enzyme containing material is cell material, the process may further comprise the step of disrupting the cell material of the bacterial strains to release the aryl acylamidase enzyme. In each case the process may still further comprise the step of separating the enzyme from the other unwanted substances, for example the cell debris and other constituent cell proteins.

The culture medium may contain any constituent which allows the bacterial strains of the present invention to produce an aryl acylamidase enzyme. Preferably however, the medium contains one or more N-acylaniline (anilides) which act as an inducer for enzyme synthesis. The one or more N-acylaniline may be selected from for example, the N-acetyl derivative of 3- or 4-hydroxyaniline, 4-ethoxyaniline or 2-, 3- or 4-methylaniline. In a preferred embodiment of the present invention however the one or more N-acylaniline is N-acetylaniline (acetanilide).

The one or more N-acylaniline may form part of either a complex medium containing naturally derived nutrient sources, such as peptones, yeast hydrolysates, etc, or a defined salts medium containing inorganic and/or simple organic nutrient sources.

The growth of the microorganisms of the present invention may take place in either batch or continuous culture. In batch culture the culture medium normally contains between about 0.01 and 0.25% (w/v) preferably between about 0.05 and 0.15% (w/v) of the one or more N-acylaniline. In continuous culture the medium is added and removed at such a rate so as to maintain the level of the one or more N-acylaniline at between about 0.001 and 0.2% (w/v) of N-acylaniline. (All of these % values refer to the amount of N-acylaniline which is available for utilisation by the bacteria.)

The culture is preferably conducted at a temperature of between about 10° C. and 45° C. most preferably between about 20° and 30° C., and at a pH of between about 6 and 9, most preferably at a pH of 6–7.5. It may be conducted under aerobic or anaerobic conditions, although the former is preferred, as it gives greater cell yields.

The cell disruption may be carried out by conventional techniques such as sonication, homogenisation or treatment with enzymes. In one preferred embodiment of the process of this invention, the cells are disrupted by enzymic treatment with lysozyme-EDTA in the presence of DNase and RNase.

Conventional enzyme isolation and purification techniques may then be used to separate the enzyme from the other unwanted substances, for example the cell debris and other constituent cell proteins present. These separations may be carried out using several properties of the enzyme, especially solubility, molecular shape molecular charge, molecular size and hydrophobic affinity. These procedures may include precipitation, particularly with ammonium sulphate, although organic solvents may be used, gel filtration on dextrans, agarose or agarose-polyacrylamide, hydrophobic chromatography, on for example alkyl agaroses, or preferably aryl agarose matrices, ion exchange chromatography, on for example DEAE cross-linked dextrans, ultracentrifugation, and/or affinity chromatography on nucleotide derivativised matrices, or on sulphonic acid substituted mono- and di-chlorotriazinyl (Procion—trade mark) dyes. In a preferred embodiment of the process of this invention the enzyme is separated from cell debris by a centrifugation step. The subsequent stage is a precipitation step, preferably using ammonium sulphate, followed by a chromatography step comprising hydrophobic chromatography, preferably on a phenyl substituted cross-linked agarose (Phenyl Sepharose—trade mark) matrix, and ion exchange chromatography, preferably on DEAE cross-linked dextran. The hydrophobic and ion-exchange chromatography may be performed in any order and as many times as required to produce the desired enzyme purity.

Ion-exchange, DEAE cross-linked dextran chromatography may be carried out using an increasing gradient of ionic strength, between 10 and 1000 mM, at a pH of between 5.5 and 8.0, but preferably with an increasing gradient between about 50 mM and 400 mM, at a pH of about 7.6.

Hydrophobic affinity chromatography may be carried out with elution using a buffer of an ionic strength below 100 mM at a pH of between 5.5 and 8.0 preferably using Tris/HCl, at pH of about 7.2, with an ionic strength of between about 10 mM and 80 mM.

It may also be carried out using a decreasing linear gradient between ionic strengths of 500 mM and 5 mM at a pH of between 5.5 and 8.0, but preferably between about 250 mM and 10 mM at a pH of about 7.6.

In a further embodiment of the present process, the enzyme separation may also comprise a gel filtration step. This filtration is preferably performed after the other chromatography steps on an agarose-acrylamide matrix although other gel filtration matrices can be used.

The aryl acylamidase enzymes produced by the process of this invention generally comprise one polypeptide chain of molecular weight between about 48,000 and 60,000 especially about 52,000.

Mutant or variant strains of Pseudomonas fluorescens NCIB 11615 (ATCC 39005) or Pseudomonas putida NCIB 11616 (ATCC 39004) may be obtained by environmental selection pressure techniques (stirpiculture), by UV irradiation or the use of mutagenic chemicals, etc. They may also be produced by genetic manipulation techniques, for example by the transfer of plasmid DNA to a multicopy host or by the excision of the chromosomal genes coding for aryl acylamidase from the cells of an aryl acylamidase producing bacteria, followed by the cloning of said genes into a suitable vector molecule. The present invention encompasses such mutant or variant strains with retained, altered or enhanced ability to produce aryl acylamidase.

Enzymes produced by the process of the present invention have many uses; however they may be particularly useful in methods of analysis of N-acylated primary aromatic amines. In particular they may be profitably used in the method of analysis described in co-pending U.K. patent application No. 8038634.

Specific embodiments of the various aspects of the invention will now be described by way of example only. In these examples the media used were as follows:

| Minimal medium | g/liter of deionised water |
| --- | --- |
| $KH_2PO_4$ | 3.0 |
| $K_2HPO_4$ | 1.0 |
| KCl | 3.0 |
| NaCl | 5.4 |
| $NH_4Cl$ | 1.1 |
| $CaCl_2.2H_2O$ | 0.01 |
| $MgCl_2.6H_2O$ | 0.1 |
| $Na_2SO_4$ | 0.02 |
| $FeCl_3.6H_2O$ | 0.0002 |

The pH of the medium was adjusted as required by the addition of either KOH or HCl.

| Complex medium | g/liter of deionised water |
| --- | --- |
| Tryptone soya broth | 20 |

Pseudomonas fluorescens NCIB 11615 (ATCC 39005) and Pseudomonas putida NCIB 11616 (ATCC 39004) were obtained from soil samples as follows:

Agar plates were prepared from the above minimal medium (1 liter) in admixture with N-acetyl-4-hydroxyaniline (1 g) and Agar (15 g). The pH of the mixture was adjusted to 6.8, using 5 M aqueous KOH, prior to autoclaving.

Soil samples (1 g) were suspended in demineralised water (5 ml) and vigorously stirred. After allowing the suspension to stand for 5 min, aliquots were plated onto the above agar plates. The plates were then incubated for up to 72 hrs and examined for growth.

Those plates showing signs of bacterial growth (ie the appearance of colonies) were subcultured to fresh medium. (It is necessary to show at this stage that the isolate is growing on the carbon source presented (N-acetyl-4-hydroxyaniline) and not on "carry-over" material from the inoculum.)

Pseudomonas fluorescens NCIB 11615 (ATCC 39005) and Pseudomonas putida NCIB 11616 (ATCC 39004) were identified by their morphological, cultural and staining characteristics when grown in batch culture on tryptone soya broth (TSB) medium and by a number of biochemical properties. The results are given in Tables 1–7.

TABLE 1

Morphological, cultural and staining characteristics of isolates, when grown for 24 hours on TSB medium.

|  | Ps. fluorescens NCIB 11615 (ATCC 39005) | Ps. putida NCIB 11616 (ATCC 39004) |
| --- | --- | --- |
| The Cell |  |  |
| Shape | Cigar Shape Rod | Cigar Shape Rod |
| Arrangement | Irregular | Irregular |
| Motility | Motile | Motile |
| Gram Stain | Negative | Negative |
| Acid Fast | Negative | Negative |
| Capsule | Negative | Negative |
| Flagella | Polar[1] | Single Polar[2] |
| Spores | None | None |
| Colonies on |  |  |

TABLE 1-continued
Morphological, cultural and staining characteristics of isolates, when grown for 24 hours on TSB medium.

| | Ps. fluorescens NCIB 11615 (ATCC 39005) | Ps. putida NCIB 11616 (ATCC 39004) |
|---|---|---|
| solid media[3] | | |
| Density | Translucent | Translucent |
| Form | Circular | Circular |
| Elevation | Convex[4] | Convex |
| Surface | Smooth | Smooth |
| Margin | Entire | Entire |
| Consistency | Mucoid | Mucoid |
| Chromogenesis | Pale Yellow | Cream |
| Size (mm) | 1.0 | 3.0 |
| Growth in liquid media | | |
| Amount of growth | Abundant | Abundant |
| Surface growth | None | None |
| Subsurface growth | Turbid | Turbid |
| Sediment | None | None |

NB:
[1]Most cells have 1-2 polar flagella although cells with up to 4 occur.
[2]Only 10% of cells have a single polar flagellum.
[3]For solid media, purified agar was added to the TSB medium to a final concentration of 1.5% (w/v).
[4]Older colonies (72 hr) become punctulate.

TABLE 2
Acid Production from Sugars

| Sugar | Ps. fluorescens NCIB 11615 (ATCC 39005) | Ps. putida NCIB 11616 (ATCC 39004) |
|---|---|---|
| Arabinose | − | + |
| Xylose | + | + |
| Rhamnose | − | − |
| Fructose | − | − |
| Galactose | − | + |
| Glucose | + | + |
| Mannose | + | − |
| Lactose | − | − |
| Maltose | − | − |
| Melibiose | − | − |
| Sucrose | − | − |
| Trehalose | − | ++ |
| Raffinose | − | − |
| Glycogen | + | + |
| Inulin | − | − |
| Starch | − | + |
| Aesculin | − | + |
| Amygdalin | − | − |
| Salicin | − | − |
| Mannitol | − | ++ |

TABLE 3
Constitutive Production of Enzymes

| Enzyme | Ps. fluorescens NCIB 11615 (ATCC 39005) | Ps. putida NCIB 11616 (ATCC 39004) |
|---|---|---|
| Oxidase | + | + |
| Catalase | + | + |
| Urease | − | − |
| NO$_3$ Reductase | + | + |
| NO$_2$ Reductase | + | − |
| Proteolytic Enzymes | + | − |
| Phenylalanine Deaminase | − | − |
| Lysine Decarboxylase | − | − |
| Arginine Dihydrolase | + | + |
| Ornithine Decarboxylase | − | − |
| Alkaline Phosphatase | + | + |
| Esterase (4-carbon) | + | + |
| Esterase Lipase (8-carbon) | + | + |
| Lipase (14-carbon) | − | − |
| Leucine arylamidase | + | + |
| Valine arylamidase | + | + |
| Cysteine arylamidase | − | + |
| Trypsin | + | + |
| Chymotrypsin | + | + |
| Acid phosphatase | − | + |
| Phosphoamidase | + | + |
| α-Galactosidase | − | − |
| β-Galactosidase | − | − |
| β-Glucuronidase | − | − |
| α-Glucosidase | − | − |
| β-Glucosidase | − | − |
| N—acetyl-β-Glucosaminidase | − | − |
| α-mannosidase | − | − |
| α-fucosidase | − | − |

Note:
[1]Gelatin liquefaction test.

TABLE 4
Christensen's Citrate Test

| Substrate | Ps. fluorescens NCIB 11615 (ATCC 39005) | Ps. putida NCIB 11616 (ATCC 39004) |
|---|---|---|
| Citrate | + | + |

TABLE 5
Tolerance towards Chemicals

| Chemical | Ps. fluorescens NCIB 11615 (ATCC 39005) | Ps. putida NCIB 11616 (ATCC 39004) |
|---|---|---|
| NaCl | 3% | 5% |
| KCN | − | − |

TABLE 6
Acidity Tests

| Test | Ps. fluorescens NCIB 11615 (ATCC 39005) | Ps. putida NCIB 11616 (ATCC 39004) |
|---|---|---|
| Litmus Milk | − | − |
| Methyl Red | − | − |

TABLE 7
Miscellaneous Tests

| Test | Ps. fluorescens NCIB 11615 (ATCC 39005) | Ps. putida NCIB 11616 (ATCC 39004) |
|---|---|---|
| Oxidation-Fermentation | Oxidation | Oxidation |
| Test for indole production | − | − |
| Test for acetyl methyl carbinol production[2] | − | − |
| Test for potential lactose fermenters[3] | − | − |
| U.V. fluorescence | + | + |

Note:
[2]Vosges-Proskauer test;
[3]Ortho-nitrophenyl-β-D-galactopyranoside test

The above results indicate that both isolates are members of the genus Pseudomonas. However, in order to fully differentiate between the two isolates, and to fully identify them beyond generic level, it is necessary to investigate their biochemical profiles with respect to their ability to utilise various compounds as sole carbon sources. The results are give in Table 8.

TABLE 8

Compounds used as sole carbon and energy sources by isolates.
(Unless otherwise stated, all compounds were used at 0.1% w/v.)

| Compound | Ps. fluorescens NCIB 11615 (ATCC 39005) | Ps. putida NCIB 11616 (ATCC 39004) |
|---|---|---|
| Adonitol | − | − |
| Dulcitol | − | − |
| Erythritol | − | − |
| Glycerol | + | + |
| Mannitol | − | + |
| Sorbitol | − | + |
| Inositol | − | − |
| Fumaric Acid | + | + |
| Succinic Acid | + | + |
| L-Malic Acid | + | + |
| 6-Aminocaproate | − | + |
| α-Ketobutyrate | − | + |
| α-Ketovalerate | + | + |
| D,L-6,8-lipoate | − | + |
| Acetanilide | + | + |
| 4-Hydroxyacetanilide | + | + |
| α-Ketoglutarate | + | + |
| Citric acid | − | + |
| Nicotinic acid | − | − |
| Oxalate | − | + |
| Phenylacetate | + | + |
| Aminophenylacetate | − | + |
| Hippuric acid | − | + |
| Acetate | + | + |
| Indolyl-3-acetate | − | + |
| Creatine | − | + |
| Creatinine | − | + |
| Sarcosine | + | + |
| Indolyl-3-acetamide | − | + |
| Acetamide | − | + |
| Lipoamide | − | + |
| Benzoic acid | + | + |
| Testosterone | − | + |
| Phenol (0.025% w/v) | − | + |

The sensitivity of each isolate towards various antibiotics was determined using standard zone inhibition techniques, employing 7 mm impregnated discs. The results are shown in Table 9.

TABLE 9

| Antibiotic | μg | Ps. fluorescens NCIB 11615 (ATCC 39005) Inhibition Zone Diameter (mm) | Ps. putida NCIB 11616 (ATCC 39004) Inhibition Zone Diameter (mm) |
|---|---|---|---|
| Ampicillin | 10 | — | — |
| Bacitracin | 8 | — | — |
| Cephaloridine | 5 | — | — |
| Chloramphenicol | 25 | — | 10 |
| Chlortetracycline | 25 | 29 | 12 |
| Cloxacillin | 5 | — | — |
| Colistin | 50 | 20 | 12 |
| Cotrimoxazole | 25 | 23 | — |
| Dimethylchlortetracycline | 25 | 32 | 12 |
| Erythromycin | 5 | — | 20 |
| Framycetin | 50 | 33 | 20 |
| Furazolidine | 50 | — | — |
| Fusidic acid | 10 | — | — |
| Gentamicin | 10 | 36 | 21 |
| Kanamycin | 30 | 36 | — |
| Linomycin | 2 | — | — |
| Methicillin | 10 | — | — |
| Nalidixic acid | 30 | 21 | — |
| Neomycin | 10 | 17 | 17 |
| Nitrofurantoin | 200 | — | — |
| Novobiocin | 5 | — | — |
| Oleandomycin | 5 | — | — |
| Oxytetracycline | 25 | 30 | 10 |
| Penicillin G | 1 | — | — |
| Penicillin V | 3 | — | — |
| Polymyxin B | 100 | 19 | 12 |
| Spiramycin | 10 | — | — |
| Streptomycin | 10 | 20 | 20[4] |
| Sulphafurazole | 500 | — | — |
| Sulphafurazole/Trimethoprim | 25 | — | — |
| Tetracycline | 25 | 30 | 12 |

Note:
[4] A spontaneous mutation in this organism allows it to express resistance to streptomycin when it has been grown on 2% TSB in the presence of 100 μg/ml streptomycin for over 48 hours.

In the following examples, enzyme activities are given in Units, defining 1 unit as 1 mole of 4-nitroacetanilide (N-acetyl-4-nitroaniline) deacylated per minute at 30° C. In a 1 ml reaction mix containing 0.5 ml $10^{-4}$ M 4-nitroacetanilide, 0.4 ml 100 mM Tris/HCl buffer (pH 8.6) and 0.1 ml sample solution.

Production of aryl acylamidase from *Pseudomonas fluorescens* NCIB 11615 (ATCC 39005) and *Pseudomonas putida* NCIB 11616 (ATCC 39004)

EXAMPLE 1

100 ml of minimal medium (as described above) containing 1 gm/liter of acetanilide and with its pH adjusted to 6.5 was placed in a 250 ml baffled flask and sterilised by autoclaving at 115° C., 10 psi, for 15 minutes. The medium was loop inoculated with *Ps. fluorescens* NCIB 11615 (ATCC 39005) and the culture was incubated at 25° C. for 48 hrs in an orbital incubator, shaken at 120 rpm. The resulting material was collected and assayed for aryl acylamidase activity. The yield of enzyme was 389 units/g dry cells.

EXAMPLE 2

The method of Example 1 was repeated except that *Ps. putida* NCIB 11616 (ATCC 39004) replaced *Ps. fluorescens* NCIB 11615 (ATCC 39005). The yield of enzyme was 183 units/g dry cells.

EXAMPLE 3

The method of Example 1 was repeated except that complex medium (as defined above) replaced minimal medium. The yield of enzyme was 476 units/g dry cells.

EXAMPLE 4

The method of Example 3 was repeated except that *Ps. putida* NCIB 11616 (ATCC 39004) replaced *Ps. fluorescens* NCIB 11615 (ATCC 39005). The yield of enzyme was 130 units/g dry cells.

Large Scale Production of Aryl acylamidase

EXAMPLE 5

(i) Seed Preparation 1 liter of minimal medium (as described above) containing 1 gm per liter of acetanilide and with its pH adjusted to 6.5 was placed in a 2 liter baffled flask and sterilised by autoclaving at 115° C., 10 psi, for 15 minutes. The medium was loop inoculated with *Ps. fluorescens* NCIB 11615 (ATCC 39005) and the culture was incubated at 25° C. for 41 hrs in an orbital incubator shaken at 120 rpm.

A 15 liter aliquot of minimal medium, pH 6.5, containing 1 gm per liter of acetanilide, was prepared in a 20 liter glass vessel. 5 ml of antifoam (polypropyleneglycol, mwt about 2000) was added and the medium was sterilised by autoclaving at 115° C., 10 psi, for 20 minutes. The sterilised medium was inoculated by the aseptic addition of the 1 liter shake flask culture and incubated at 25° C. for 36 hrs, with an aeration rate of 12 liter bottom air per minute.

(ii) Large Scale Medium Preparation

Tryptone soya broth (8000 g) and acetanilide (400 g) were added to demineralised water (400 liter) in a stainless steel fermentation vessel (500 liter) of the Porton design (C. G. T. Evans, et al., Methods in Microbiology, Vol 2, Ch. 13, pp 277–323, Ed. J. R. Norris and D. Ribbons, Academic Press, London). The medium was sterilised in situ by heating the vessel at 121° C., 10 psi, for 30 minutes.

(iii) Incubation

The complex medium was inoculated by the aseptic addition of 15 liters of seed culture. The 400 liter culture was aerated with pre-sterilised bottom air at a rate of 300 liters per minute. The temperature of the culture was maintained at 25° C. and it was stirred mechanically at 250 rpm. Foaming was controlled by the aseptic addition, as necessary, of pre-sterilised polypropyleneglycol (mwt 2000), and the effluent gas was monitored for percent content of $CO_2$. The pH of the culture was allowed to fluctuate naturally until the pH of the maturing culture reached a level of 7.6. It was then controlled at this value by addition of 20% $H_3PO_4$.

(iv) Harvesting

After 20 hours incubation the air to the culture vessel was switched off and the temperature of the culture decreased to 15° C. The culture was then centrifuged under non-sterile but chemically clean conditions, via a chilled plate exchanger, through two De Laval centrifuges running in parallel (flow rate 50–60 liter/hour). Stirring and pH control was maintained until the level of the culture fell below that of the impellor. During centrifugation, the vessel was held under top air, effectively creating an anaerobic state in the culture. The supernatant was pumped to a holding tank, then to a destruct tank, where it was destroyed by formalising and heating before disposal. The bacterial cells was collected and weighed. 7.21 Kg of wet cell paste containing 370,000 units of aryl acylamidase was obtained.

EXAMPLE 6

1 g (wet weight) of bacterial cells, obtained by the methods of Example 5, were suspended in 5 ml potassium phosphate buffer, pH 7.6, ionic strength 0.1 M. Deoxyribonuclease (DNase) and ribonuclease (RNase) were added (approx 1 mg each) and the preparation mixed gently by stirring. EDTA (1.0 ml of a 0.2 M solution) was added followed by 1 ml lysozyme (10 mg/ml). Mixing was continued for a further 5 minutes or until viscosity was seen to increase, indicating lysis. When lysis was complete 1 ml 0.5 M $MgCl_2.6H_2O$ was added to activate nuclease activity and reduce viscosity.

EXAMPLE 7

A cell suspension was prepared as in Example 6 and DNase, RNase, EDTA and lysozyme added. After gently mixing the preparation it was allowed to stand at 4° C. for 10 minutes. 0.5 ml of 10% (w/v) sodium dodecyl sulphate (SDS) was added and the preparation allowed to stand at 37° C. for a further 10 minutes. When lysis was complete, $MgCl_2$ was added as in Example 6.

EXAMPLE 8

A cell suspension was prepared as in Example 6. 1 ml of 5 M NaCl and 1 ml of 0.2 M EDTA were added, followed by 1 ml of lysozyme (conc 10 mg/ml). The preparation was stirred gently at ambient temperature for 15 minutes. After this time 0.5 ml of the non-ionic surfactant, Triton X-100 (trade mark) was added. Mixing was continued for a further 5 minutes and the preparation was then allowed to stand for 4 hours or until lysis occurred. $MgCl_2$ was then added as in Example 6.

EXAMPLE 9

1 g (wet weight) of bacterial cells prepared by the method of Example 5 were suspended in 10 ml of potassium phosphate buffer (pH 7.6) and cooled to 0° C. Preparations were sonicated using a Soniprobe type 7532B (supplied by Dawe Instruments Ltd) at 5A, 20 kc/sec, for up to 5 minutes. Isolates were sonicated for 30 second periods, each sonication being followed by a cooling period of about 2 minutes. The temperature was not allowed to rise above 10° C.

Isolation of Enzyme

EXAMPLE 10

Bacterial cells were prepared by the method of Example 5. The cells (100 grams) were disrupted by enzymic treatment with lysozyme-EDTA (the method of Example 6), and the cell debris removed by centrifugation to yield a cell extract containing 0.64 units/mg of protein.

The cell extract was then successively purified by ammonium sulphate precipitation, desalting on a cross-linked dextran (Sephadex G-25, trade mark) in 50 mM phosphate buffer pH 7.6, chromatography on DEAE cross-linked dextran (DEAE Sephadex, trade mark) with a 41 increasing, linear gradient between 50 and 400 mM phosphate, pH 7.6, and gel filtration on agarose-acrylamide in 50 mM phosphate, pH 7.6.

The resulting yields, based on the cell extract, and specific activities are given in Table 10.

TABLE 10

| Purification step | Yield (%) | Specific Activity (Units/mg protein) |
|---|---|---|
| Cell Extract | 100 | 0.64 |
| Ammonium Sulphate precipitation | 96 | 1.47 |
| Sephadex G-25 eluate | 79 | 5.69 |
| DEAE Sephadex eluate | 54 | 24.06 |
| Agarose-acrylamide eluate | 45 | 163.02 |

EXAMPLE 11

Bacterial cells were prepared by the method of Example 5. The cells (300 grams) were disrupted by enzymic treatment with lysozyme-EDTA (the method of Example 6) and cell debris removed by centrifugation to yield a cell extract containing 0.37 units/mg of protein.

The cell extract was then successively purified, firstly by ammonium sulphate precipitation, followed by desalting on cross-linked dextran (Sephadex G-24, trade mark) in 100 mM phosphate buffer, pH 7.6. The eluate was chromatographed on DEAE cross-linked dextran (DEAE Sephadex, trade mark) with a 41 increasing, linear gradient between 50 and 400 mM phosphate pH 7.6, followed by hydrophobic chromatography on phenyl substituted cross-linked agarose (Phenyl Sepharose, trade mark) in 10 mM tris/HCl, pH 7.2. The eluate was chromatographed on DEAE cross-linked dextran (DEAE Sephadex, trade mark) with a 500 ml increasing, linear grdient between 10 and 400 mM phosphate, pH 7.6, followed by hydrophobic chromatography on phenyl substituted cross-linked agarose (Phenyl Sepharose, trade mark) in 10 mM tris/HCl, pH 7.2. The eluate was chromatographed on DEAE cross-linked dextran (DEAE Sephadex, trade mark) with a 500 ml increasing, linear gradient between 10 and 400 mM phosphate, pH 7.6, followed by hydrophobic chromatography on phenyl substituted cross-linked agarose (Phenyl Sepharose, trade mark) with a decreasing, linear gradient between 250 mM phosphate pH 7.6 and 10 mM tris/HCl, pH 7.2, followed by subsequent elution with 10 mM tris/HCl, pH 7.2.

The resulting yields; based on the cell extract, and specific activities are given in Table 11.

TABLE 11

| Purification step | Yield (%) | Specific Activity (Units/mg protein) |
|---|---|---|
| Cell Extract | 100 | 0.37 |
| Ammonium sulphate precipitation | 87 | 0.83 |
| Sephadex G-25 eluate | 42 | 1.37 |
| DEAE - Sephadex eluate | 37 | 23.81 |
| Phenyl - Sepharose eluate | 21 | 24.27 |
| Agarose - acrylamide eluate | 17 | 75.84 |
| DEAE - Sephadex eluate | 16 | 145.06 |
| Phenyl - Sepharose eluate | 10 | 307.17 |

The purified enzyme was homogeneous, and a monomer comprising one unit of molecular weight about 52,500.

EXAMPLE 12

Bacterial cells were prepared by the method of Example 5. The cells (200 grams) were disrupted by enzymic treatment with lysozyme-EDTA (the method of Example 6) and cell debris removed by centrifugation to yield a cell extract containing 0.29 units/mg of protein.

The cell extract was then successively purified, firstly by ammonium sulphate precipitation, followed by desalting on a cross-linked dextran (Sephadex G-25, trade mark) in 100 mM phosphate buffer, pH 7.6. The eluate was chromatographed on DEAE cross-linked dextran (DEAE Sephadex, trade mark) with a 31 increasing, linear gradient between 100 and 400 mM phosphate, pH 7.6, followed by hydrophobic chromatography on phenyl substituted cross-linked agarose (Phenyl Sepharose, trade mark) with a 500 ml decreasing, linear gradient between 300 mM phosphate, pH 7.6, and 10 mM tris/HCl, pH 7.2. The eluate was chromatographed by gel filtration on agarose-acrylamide in 10 mM tris/HCl, pH 7.2.

The resulting yields, based on the cell extract, and specific activities are given in Table 12.

TABLE 12

| Purification step | Yield (%) | Specific Activity (Units/mg protein) |
|---|---|---|
| Cell Extract | 100 | 0.29 |
| Ammonium sulphate precipitation | 100 | 1.01 |
| Sephadex G-25 eluate | 100 | 1.19 |
| DEAE Sephadex eluate | 98 | 6.57 |
| Phenyl Sepharose eluate | 65 | 88.09 |
| Agarose-acrylamide eluate | 50 | 201.40 |

EXAMPLE 13

Bacterial cells were prepared by the method of Example 5. The cells (2 kg) were then suspended in 4 dm³ 100 mM potassium phosphate buffer, pH 7.6, and treated with a mixture of DNase (5 mg), RNase (5 mg) and 0.2 M EDTA (200 ml). The preparation was stirred gently on a magnetic stirrer and then 20 ml aqueous lysozyme solution (50 mg ml$^{-1}$) was added and the stirring was continued for 10 mins until viscosity increased, indicating cell lysis. At this point MgCl$_2$.6H$_2$O (0.5 M, 200 ml) was added to the reaction mixture and the stirring was continued until the viscosity decreased. Solid ammonium sulphate was then added to a concentration of 15% saturation and the preparation was centrifuged in a Sorval RC3B centrifuge (H-6000 rotor) at 4,700 g and 4° C., for 5 hrs. When the centrifugation was complete the supernatant was immediately decanted and then, consecutively, fractionated with ammonium sulphate (between 15 and 25% saturation) and centrifuged for 16 hrs. The decanting, fractionation (between 25 and 40% saturation) and centrifugation (4 hrs) was repeated. The supernatant was then decanted and discarded and the precipitate from the final centrifugation was resuspended in 500 ml 100 mM potassium phosphate, pH 7.6, using a Silverson laboratory mixer fitted with an emulsor screen.

A 6 dm³ Sephadex G25 (coarse) column (94×9.0 cm) was pre-equilibrated with 100 mM potassium phosphate, pH 7.6, and the enzyme preparation was loaded onto it with an upwards flow rate of 2 dm³ hr$^{-1}$. The column was eluted at 2 dm³ hr$^{-1}$ with 100 mM potassium phosphate, pH 7.6. The protein content of the eluate was monitored at 280 nm and when the protein level in the eluate began to rise (accompanied by an increase in enzyme activity as confirmed by specific assay), the eluate was collected as one fraction.

A 5 dm³ DEAE Sephadex A50 column (33×14 cm) was pre-equilibrated with 100 mM potassium phosphate, pH 7.6, and the Sephadex G25 pool containing the amidase was loaded onto it, with a downwards flow rate of 900 cm³ hr$^{-1}$. The column was washed with 12.5 dm³ 100 mM potassium phosphate, pH 7.6, and then eluted at 800 cm³ hr$^{-1}$ with a 20 dm³ linear increasing gradient (10 dm³+10 dm³) between 100 and 400 mM potassium phosphate, pH 7.6, 300 cm³ fractions were collected. Fractions 40 to 50 were pooled for peak enzyme activity.

A 500 cm³ phenyl Sepharose CL-4B column (8×9.0 cm) was pre-equilibrated with 300 mM potassium phosphate, pH 7.6 and the DEAE Sephadex pool containing the amidase was loaded onto it with a downwards flow rate of 400 cm³ hr$^{-1}$. The column was washed with 1500 cm³ 100 mM tris-HCl, pH 7.6, at 100 cm³ hr$^{-1}$ and then eluted with a 3 dm³ linear decreasing gradient (1.5 dm³+1.5 dm³) between 100 and 10 mM tris-HCl, pH 7.6, at 300 cm³ hr$^{-1}$. 100 cm³ fractions were collected. The column was then eluted with 3 dm³ 10 mM tris-HCl, pH 7.6, at 200 cm³ hr$^{-1}$ and 100 cm³ fractions were collected. Fractions 21 to 37 were pooled for peak enzyme activity.

The phenyl Sepharose pool containing the amidase was concentrated by ultrafiltration using an Amicon model 202 concentrator, under top nitrogen pressure, with a 62 mm diameter PM10 membrane (nominal cutoff M.W. = 10,000). The pool was concentrated to a volume of 40 cm³.

A 2 dm³ AcA 44 Ultrogel column (94×5.2 cm) was pre-equilibrated with 100 mM tris-HCl, pH 7.6, and the concentrated enzyme solution was loaded onto it with an upwards flow rate of 60 cm³ hr⁻¹. The column was eluted with 100 mM tris-HCl, pH 7.6, at 60 cm³ hr⁻¹ and 60 cm³ fractions were collected. Fractions 16 to 18 were pooled for peak enzyme activity.

A 100 cm³ DEAE Sephadex A50 column (12×3.5 cm) was pre-equilibrated with 100 mM tris-HCl, pH 7.6, and the AcA 44 pool containing the amidase was loaded onto it with a downwards flow rate of 20 cm³ hr⁻¹. The column was washed with 400 cm³ 100 mM potassium phosphate, pH 7.6, and then eluted at 20 cm³ hr⁻¹ with a 1 dm³ linear increasing gradient (500 cm³×500 cm³) between 100 and 400 mM potassium phosphate, pH 7.6. 10 cm³ fractions were collected and fractions 29 to 35 were pooled for peak enzyme activity.

A 50 cm³ phenyl Sepharose CL-4B column (6.5×3.2 cm) was pre-equilibrated with 100 mM potassium phosphate, pH 7.6, and the second DEAE Sephadex pool was loaded onto it with a downwards flow rate of 150 cm³ hr⁻¹. The column was washed with 100 cm³ 100 mM potassium phosphate, pH 7.6, 100 cm³ 100 mM tris-HCl, pH 7.6, and 100 cm³ 80 mM tris-HCl, pH 7.6. It was then eluted with a 300 cm³ linear decreasing gradient (150 cm³+150 cm³) between 80 and 20 mM tris-HCl, pH 7.6, with a flow rate of 150 cm³ hr⁻¹. The column was then eluted with 200 cm³ 20 mM Tris-HCl, pH 7.6 and 2 cm³ fractions were collected. Fractions 150 to 170 were pooled for peak enzyme activity.

The resulting yields, based on the cell extract, and specific activities are given in Table 13.

TABLE 13

| Purification step | Yield (%) | Specific Activity (Units/mg protein) |
|---|---|---|
| Cell Extract | 100 | 0.19 |
| Ammonium sulphate precipitation | 85 | 0.83 |
| DEAE Sephadex | 75 | 4.58 |
| Phenyl Sepharose | 63 | 48.33 |
| Ultrogel AcA 44 | 61 | 117.84 |
| DEAE Sephadex | 51 | 172.91 |
| Phenyl Sepharose | 10 | 319.17 |

Native molecular weight of enzyme

The native molecular weight of the amidase prepared by the method of Example 13 was determined after chromatography by gel filtration on AcA 44 Ultrogel. The column was calibrated using protein standards of known molecular weight. In order to determine elution volume without overlapping of protein peaks, samples were chromatographed in groups:
group one, bovine serum albumin, chymotrypsinogen A, cytochrome c;
group two, ovalbumin, myoglobin;
group three, aryl acylamidase.

The void volume of the column was determined using blue dextran 2000 and the total volume using bromophenol blue dye. The molecular weight of the amidase was determined from a standard curve of Kav versus log 10 molecular weight.

Kav was determined for each protein using the following equation, $$Kav = \frac{V_e - V_o}{V_t - V_o}$$

where
$V_t$=elution volume
$V_o$=void volume
$V_t$=total volume

The elution position of aryl acylamidase represents a native molecular weight of 52,000 daltons.

Subunit molecular weight of enzyme

The subunit molecular weight of aryl acylamidase prepared by the method of Example 13 was determined by comparing its electrophoretic mobility with those of protein standards. The standards used were phosphorylase B (100,000 daltons), bovine serum albumin (68,000 daltons), ovalbumin (45,000 daltons), carbonic anhydrase (29,000 daltons), soya trypsin inhibitor (21,500 daltons) and lysozyme (14,300 daltons). The electrophoretic mobility of the standards was expressed as a percentage of the corresponding mobility of a bromophenol blue marker. A calibration graph of log 10 molecular weight versus electrophoretic mobility was used to determine the molecular weight of the amidase.

A subunit molecular weight of 52,500 daltons was indicated.

Isoelectric Focusing

The isoelectric point of the amidase enzyme prepared by the method of Example 13 was found to be pH 7.2 by isoelectric focusing.

What I claim is:

1. A process for producing an aryl acylamidase enzyme which comprises
   a. culturing bacteria of one of the strains *Pseudomonas fluorescens* ATCC 39005 or arylacylamidase producing mutants or variants thereof, or *Pseudomonas putida* ATCC 39004 or aryl acylamidase producing mutants or variants thereof in a culture medium in which said bacterial strains produce aryl acylamidase, to produce an enzyme containing material consisting of the aryl acylamidase enzyme and other unwanted substances, and
   b. collecting the enzyme containing material.

2. A process according to claim 1 wherein the enzyme containing material is cell material.

3. A process according to claim 2 further comprising the step of disrupting the collected cell material to release the aryl acylamidase enzyme and other cell constituents.

4. A process according to claim 3 further comprising the step of separating the aryl acylamidase enzyme from the other cell constituents.

5. A process according to claim 1 wherein the culture medium contains at least one N-acylaniline.

6. A process according to claim 5 wherein the at least one N-acylaniline comprises N-acetylaniline.

7. A process according to claim 5 wherein the at least one N-acylaniline comprises at least one N-acylaniline selected from the group consisting of N-acetyl-3-hydroxyaniline, N-acetyl-4-hydroxyaniline, N-acetyl-4-ethoxyaniline, N-acetyl-2-methylaniline, N-acetyl-3-methylaniline and N-acetyl-4-methylaniline.

8. A process according to claim 5 wherein the bacteria are cultured in batch culture and the culture medium contains between 0.01 and 0.25% (w/v) of at least one N-acylaniline which is available for utilisation by the bacteria.

9. A process according to claim 8 wherein the culture medium contains between 0.05 and 0.15% (w/v) of at least one N-acylaniline.

10. A process according to claim 5 wherein the bacteria are cultured in continuous culture and the culture medium contains between 0.001 and 0.2% (w/v) of at least one N-acylaniline which is available for utilisation by the bacteria.

11. A process according to claim 5 wherein the culture medium is a complex medium.

12. A process according to claim 1 wherein the temperature of the culture medium is between 10° and 45° C.

13. A process according to claim 12 wherein the temperature is between 20° and 30° C.

14. A process according to claim 1 wherein the pH of the culture medium is between 6 and 9.

15. A process according to claim 14 wherein the pH is between 6 and 7.5.

16. A process according to claim 1 wherein the bacteria are cultured under aerobic conditions.

17. A process according to claim 3 wherein the collected cell material is disrupted by enzymic treatment of the material with a mixture of lysozyme and EDTA in the presence of deoxyribonuclease and ribonuclease.

18. A process according to claim 4 wherein the aryl acylamidase enzyme is separated from the other cell constituents by a method of separation which includes at least one chromatographic procedure.

19. A process according to claim 18 wherein the method of separation includes the steps of precipitation, hydrophobic chromatography and ion exchange chromatography.

20. A process according to claim 19 wherein the hydrophobic chromatography is performed on a phenyl substituted cross linked agarose matrix using Tris-HCl (pH of about 7.2) with an ionic strength of between 10 mM and 80 mM.

21. A process according to claim 19 wherein the hydrophobic chromatography is performed on a phenyl substituted cross linked agarose matrix using a decreasing linear gradient of ionic strength between 250 and 10 mM at a pH of about 7.6

22. A process according to claim 19 wherein the ion exchange chromatography is performed on a DEAE cross linked dextran matrix using an increasing gradient of ionic strength between 50 and 400 mM at a pH of about 7.6.

23. A process according to claim 19 wherein the method of separation further includes the step of gel filtration.

24. A substantially pure aryl acylamidase enzyme whenever prepared by a process according to claim 4, said enzyme being an enzymatic catalyst for the hydrolysis of N-acetyl-4-hydroxyaniline to 4-hydroxyaniline.

25. A biologically pure culture of the micro-organism *Pseudomonas fluorescens*, deposited as ATCC 39005, said culture having the ability to produce an aryl acylamidase enzyme upon culturing in a suitable culture medium, and biologically pure aryl acylamidase producing mutants or variants thereof.

26. A biologically pure culture of the micro-organism *Pseudomonas putida*, deposited as ATCC 39004, said culture having the ability to produce an aryl acylamidase enzyme upon culturing in a suitable culture medium, and biologically pure aryl acylamidase producing mutants and variants thereof.

* * * * *